United States Patent
Morsi

(10) Patent No.: US 10,314,600 B2
(45) Date of Patent: Jun. 11, 2019

(54) CLOT REMOVAL DEVICE AND METHOD OF USING SAME

(71) Applicant: NOHA, LLC, Houston, TX (US)

(72) Inventor: Hesham Morsi, Houston, TX (US)

(73) Assignee: NOHA, LLC, Houston, TX (US)

( * ) Notice: Subject to any disclaimer, the term of this patent is extended or adjusted under 35 U.S.C. 154(b) by 434 days.

(21) Appl. No.: 15/093,552

(22) Filed: Apr. 7, 2016

(65) Prior Publication Data

US 2016/0213388 A1    Jul. 28, 2016

Related U.S. Application Data

(63) Continuation of application No. 13/654,016, filed on Oct. 17, 2012, now Pat. No. 9,358,022.
(Continued)

(51) Int. Cl.
*A61B 17/221*    (2006.01)
*A61B 17/22*    (2006.01)
(Continued)

(52) U.S. Cl.
CPC ...... *A61B 17/22032* (2013.01); *A61B 17/221* (2013.01); *A61F 2/013* (2013.01); *A61B 2017/00287* (2013.01); *A61B 2017/00867* (2013.01); *A61B 2017/2212* (2013.01); *A61B 2017/2215* (2013.01);
(Continued)

(58) Field of Classification Search
CPC ........ A61B 17/221; A61B 2017/00287; A61B 2017/2212; A61B 2017/2215; A61F 2/01; A61F 2/013; A61F 2002/018; A61F 2230/0067

See application file for complete search history.

(56) References Cited

U.S. PATENT DOCUMENTS 4,484,579 A    11/1984   Meno et al.
4,501,264 A     2/1985   Rockey
(Continued)

FOREIGN PATENT DOCUMENTS

DE       10010467 B2    9/2001
NO      2007089897 A2   8/2007
WO    WO 2011/034718    3/2011

OTHER PUBLICATIONS

"Sentinel Cerebral Protection System Specifications and Ordering Guide," Claret Medical, URL: http://www.claretmedical.com/pdf/2018/PL-11538_A-US-Sentinel-Spec-Sheet_Example-Label_Ordering-Info.pdf accessed on Feb. 20, 2018.
(Continued)

*Primary Examiner* — Ryan J. Severson
*Assistant Examiner* — Christian D Knauss
(74) *Attorney, Agent, or Firm* — Norton Rose Fulbright US LLP

(57) ABSTRACT

A minimally invasive endovascular device for treating a blocked or obstructed biological lumen, such as a blood vessel fully or partially obstructed by deposits of biological matters in or non-biological matters. Certain embodiments of the present invention comprise two capture members that are configured to be placed on either side of the obstruction and enclose around the obstruction for removal. Embodiments of the present invention also provide methods for implementing an endovascular device according to aspects of the present invention.

22 Claims, 8 Drawing Sheets

Related U.S. Application Data

(60) Provisional application No. 61/688,784, filed on May 21, 2012.

(51) Int. Cl.
*A61F 2/01* (2006.01)
*A61B 17/00* (2006.01)
*A61B 90/00* (2016.01)

(52) U.S. Cl.
CPC ............. *A61B 2017/22035* (2013.01); *A61B 2017/22038* (2013.01); *A61B 2017/22051* (2013.01); *A61B 2017/22072* (2013.01); *A61B 2017/22079* (2013.01); *A61B 2017/22094* (2013.01); *A61B 2090/3966* (2016.02); *A61F 2002/018* (2013.01); *A61F 2230/0067* (2013.01)

(56) References Cited

U.S. PATENT DOCUMENTS

| | | | |
|---|---|---|---|
| 4,693,721 A | 9/1987 | Ducheyne | |
| 4,696,668 A | 9/1987 | Wilcox | |
| 4,998,539 A | 3/1991 | Delsanti | |
| 5,011,488 A | 4/1991 | Ginsburg | |
| 5,057,092 A | 10/1991 | Webster, Jr. | |
| 5,549,626 A * | 8/1996 | Miller | A61F 2/01 606/191 |
| 5,814,064 A * | 9/1998 | Daniel | A61B 17/22031 606/159 |
| 5,868,708 A | 2/1999 | Hart et al. | |
| 5,868,779 A | 2/1999 | Ruiz | |
| 5,904,698 A | 5/1999 | Thomas et al. | |
| 5,947,985 A | 9/1999 | Imran | |
| 6,129,739 A * | 10/2000 | Khosravi | A61F 2/01 606/194 |
| 6,152,946 A | 11/2000 | Broome et al. | |
| 6,159,230 A | 12/2000 | Samuels | |
| 6,238,412 B1 | 5/2001 | Dubrul et al. | |
| 6,319,242 B1 | 11/2001 | Patterson et al. | |
| 6,346,116 B1 | 2/2002 | Brooks et al. | |
| 6,544,279 B1 * | 4/2003 | Hopkins | A61F 2/01 606/194 |
| 6,547,760 B1 | 4/2003 | Samson et al. | |
| 6,592,616 B1 | 7/2003 | Stack et al. | |
| 6,595,988 B2 | 7/2003 | Wittenberger et al. | |
| 6,935,139 B2 | 8/2005 | Nagayama et al. | |
| 6,974,469 B2 | 12/2005 | Broome et al. | |
| 7,001,407 B2 | 2/2006 | Hansen et al. | |
| 7,252,650 B1 | 8/2007 | Andrews et al. | |
| 7,285,126 B2 | 10/2007 | Sepetka et al. | |
| 7,572,272 B2 | 8/2009 | Denison et al. | |
| 7,618,434 B2 | 11/2009 | Santra et al. | |
| 7,837,704 B2 | 11/2010 | Brady et al. | |
| 8,123,779 B2 | 2/2012 | Demond et al. | |
| 8,372,108 B2 | 2/2013 | Lashinski | |
| 8,876,796 B2 | 11/2014 | Fifer et al. | |
| 8,974,489 B2 | 3/2015 | Lashinski | |
| 9,017,364 B2 | 4/2015 | Fifer et al. | |
| 9,055,997 B2 | 6/2015 | Fifer et al. | |
| 9,259,306 B2 | 2/2016 | Fifer et al. | |
| 9,326,843 B2 | 5/2016 | Lee et al. | |
| 9,345,565 B2 | 5/2016 | Fifer et al. | |
| 9,492,264 B2 | 11/2016 | Fifer et al. | |
| 9,636,205 B2 | 5/2017 | Lee et al. | |
| 2001/0044632 A1 | 11/2001 | Daniel et al. | |
| 2002/0026211 A1 | 2/2002 | Khosravi et al. | |
| 2002/0049408 A1 | 4/2002 | Van Moorlegem et al. | |
| 2002/0188276 A1 | 12/2002 | Evans et al. | |
| 2003/0055377 A1 | 3/2003 | Sirhan et al. | |
| 2003/0114879 A1 | 6/2003 | Euteneuer et al. | |
| 2003/0195537 A1 | 10/2003 | Dubrul et al. | |
| 2003/0236533 A1 | 12/2003 | Wilson et al. | |
| 2004/0002730 A1 | 1/2004 | Denison et al. | |
| 2004/0006366 A1 | 1/2004 | Huter et al. | |
| 2004/0093009 A1 | 5/2004 | Denison et al. | |
| 2004/0220609 A1 | 11/2004 | Douk et al. | |
| 2005/0003334 A1 | 1/2005 | Titus | |
| 2005/0038468 A1 | 2/2005 | Panetta et al. | |
| 2005/0043746 A1 | 2/2005 | Pollak et al. | |
| 2005/0043756 A1 | 2/2005 | Lavelle et al. | |
| 2005/0119691 A1 | 6/2005 | Daniel et al. | |
| 2005/0171566 A1 * | 8/2005 | Kanamaru | A61B 17/22 606/159 |
| 2005/0267491 A1 | 12/2005 | Kellett et al. | |
| 2006/0089664 A1 | 4/2006 | Hansen et al. | |
| 2006/0206197 A1 | 9/2006 | Morsi | |
| 2006/0229645 A1 | 10/2006 | Bonnette et al. | |
| 2006/0229658 A1 | 10/2006 | Stivland | |
| 2006/0247674 A1 | 11/2006 | Roman | |
| 2006/0271093 A1 | 11/2006 | Holman et al. | |
| 2007/0185500 A1 | 8/2007 | Martin et al. | |
| 2007/0198047 A1 | 8/2007 | Schon et al. | |
| 2007/0208367 A1 | 9/2007 | Fiorella et al. | |
| 2007/0225749 A1 | 9/2007 | Martin et al. | |
| 2008/0058860 A1 | 3/2008 | Demond et al. | |
| 2008/0077175 A1 | 3/2008 | Palmer | |
| 2008/0167678 A1 | 7/2008 | Morsi | |
| 2008/0243170 A1 | 10/2008 | Jenson et al. | |
| 2008/0300621 A1 | 12/2008 | Hopkins et al. | |
| 2009/0062840 A1 | 3/2009 | Angel | |
| 2009/0105722 A1 | 4/2009 | Fulkerson et al. | |
| 2009/0182370 A1 | 7/2009 | Volobuyev et al. | |
| 2009/0240238 A1 | 9/2009 | Grodrian et al. | |
| 2009/0299393 A1 | 12/2009 | Martin et al. | |
| 2010/0036312 A1 | 2/2010 | Krolik et al. | |
| 2010/0217304 A1 * | 8/2010 | Angel | A61F 2/013 606/200 |
| 2011/0015220 A1 | 1/2011 | Linz et al. | |
| 2011/0106138 A1 | 5/2011 | Hancock et al. | |
| 2011/0125181 A1 | 5/2011 | Brady et al. | |
| 2011/0137334 A1 | 6/2011 | Anderson et al. | |
| 2011/0202088 A1 | 8/2011 | Eckhouse et al. | |
| 2011/0257678 A1 | 10/2011 | Salahieh et al. | |
| 2011/0264135 A1 | 10/2011 | Demond et al. | |
| 2012/0172920 A1 * | 7/2012 | Fifer | A61F 2/013 606/200 |
| 2012/0197285 A1 | 8/2012 | Martin et al. | |
| 2013/0184739 A1 * | 7/2013 | Brady | A61B 17/221 606/200 |
| 2013/0231694 A1 | 9/2013 | Lashinski | |
| 2014/0243877 A9 | 8/2014 | Lee et al. | |
| 2015/0209131 A1 | 7/2015 | Fifer et al. | |
| 2015/0335416 A1 | 11/2015 | Fifer et al. | |
| 2017/0042658 A1 | 2/2017 | Lee et al. | |

OTHER PUBLICATIONS

International Search Report and Written Opinion issued in PCT/US2013/064988, dated May 2, 2014.

European Search Report for European Application 08873576.6 dated Dec. 1, 2011.

* cited by examiner

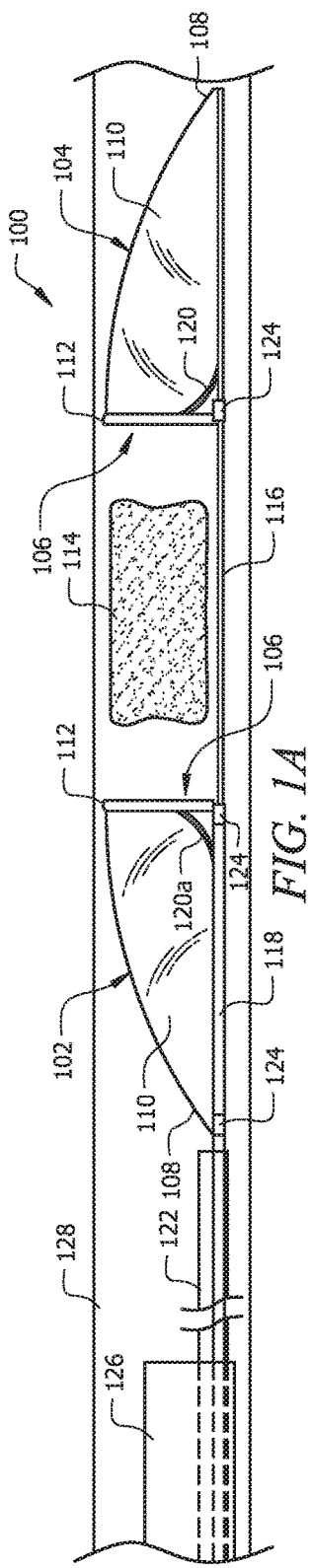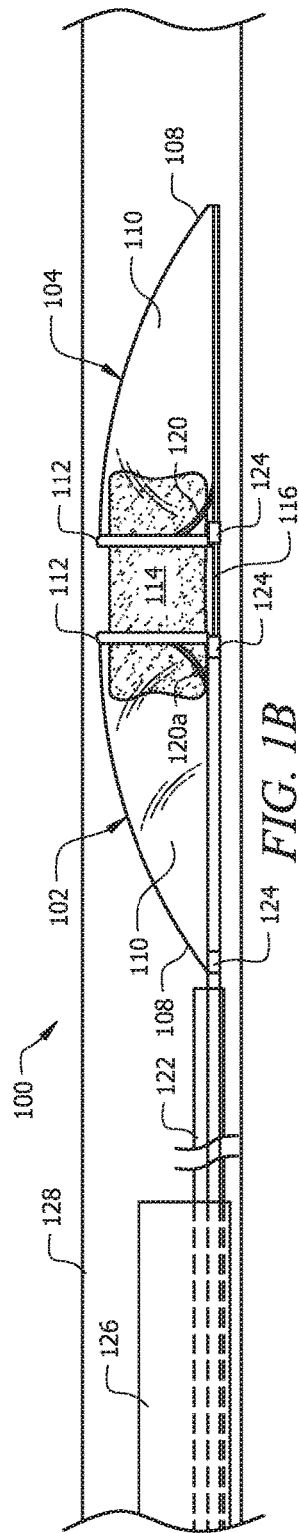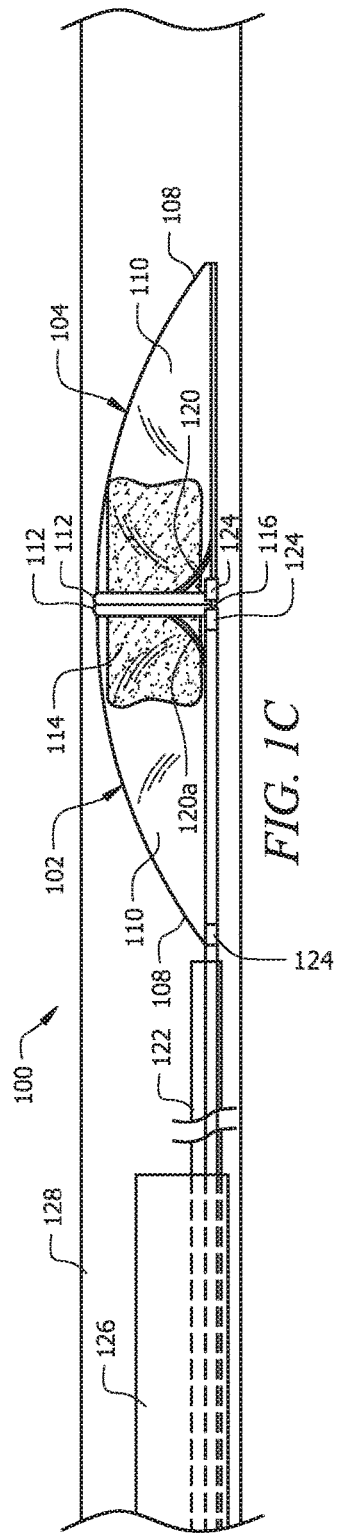

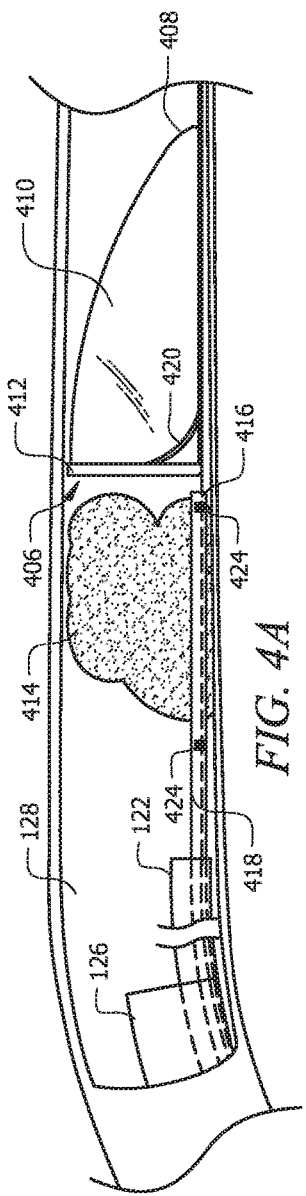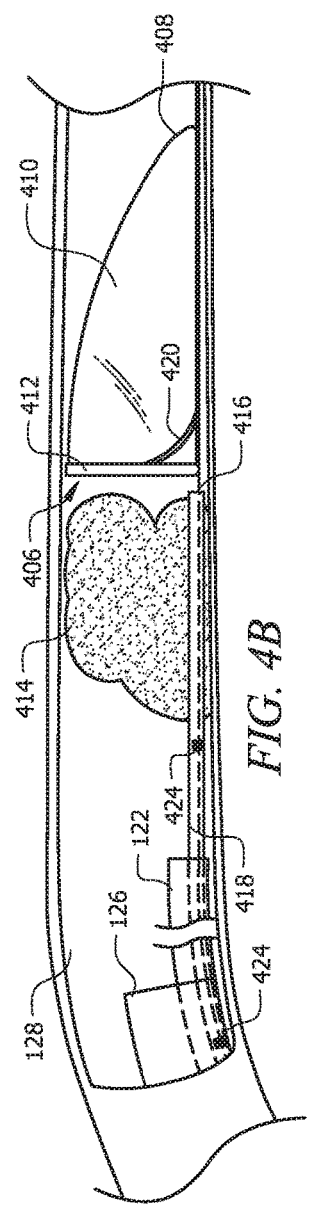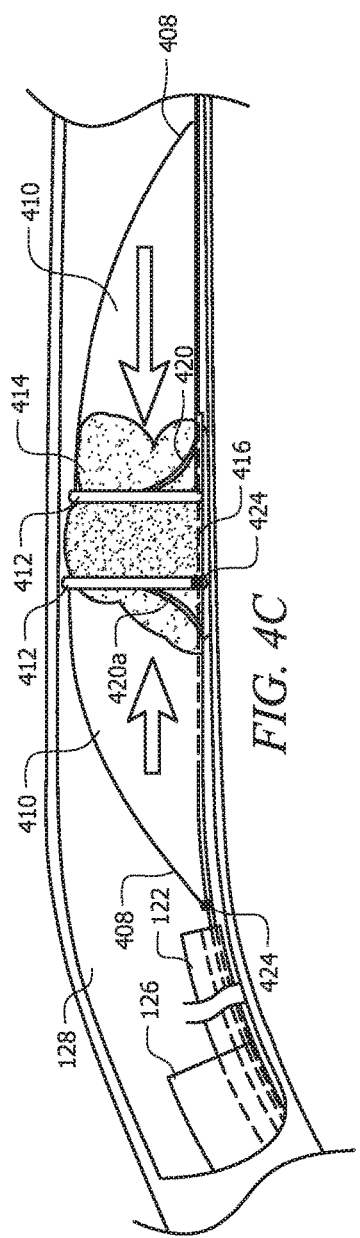

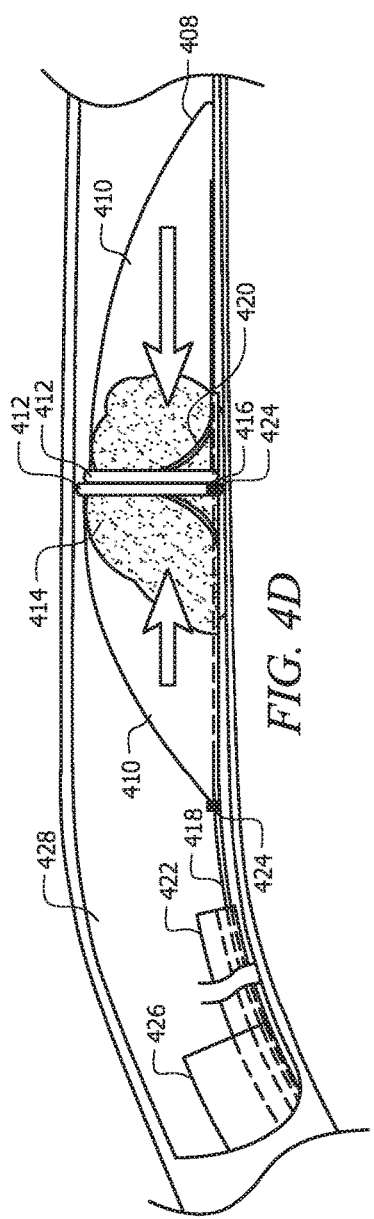
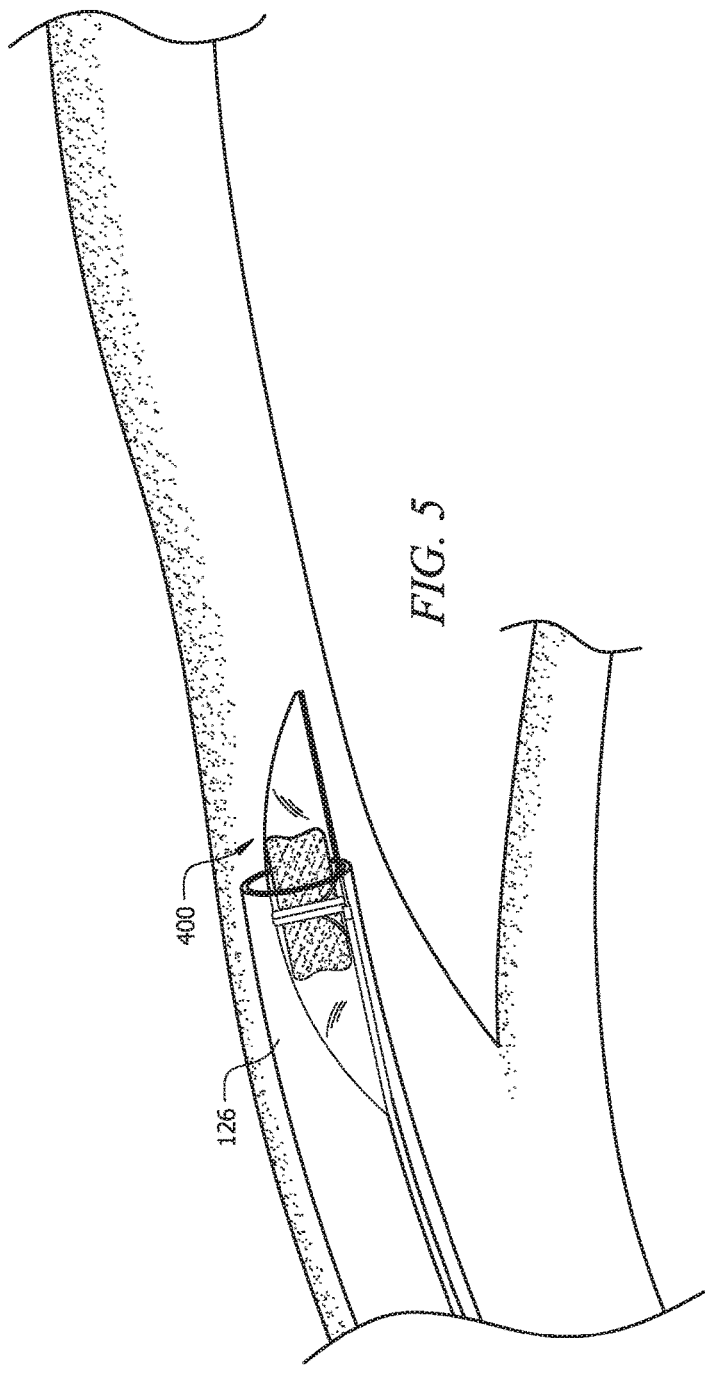

CLOT REMOVAL DEVICE AND METHOD OF USING SAME

CROSS-REFERENCE TO RELATED APPLICATIONS

This application is a continuation of U.S. patent application Ser. No. 13/654,016 filed Oct. 17, 2012, which claims the benefit of priority to U.S. Provisional Application No. 61/688,784, filed on May 21, 2012, the disclosures of which are incorporated herein by reference in their entirety.

TECHNICAL FIELD

Embodiments of the present invention relate generally to medical devices and methods of using same, and more specifically, to medical devices for treating or treating an occluded biological lumen, such as an embolus or clot in a blood vessel.

BACKGROUND OF THE INVENTION

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as any admission of prior art.

There are many reasons a blood vessel becomes blocked or obstructed. One common way is from deposition of thrombus or clot inside the lumen of the blood vessels which can restrict the antegrade blood flow through the lumens of these blood vessels to the body tissues. Because arterial blockages reduce blood flow through the affected vessel, any blockage or obstruction can lead to many serious medical complications as tissue relying on the blood's supply of oxygen may become damaged due to the decrease in the oxygen amount. For instance in the brain circulation this can lead to stroke with loss of vital brain functions and/or death, while in the heart it can lead heart attack due to damage of the heart muscle with significant impairment of its ability to pump blood to the body organ which can eventually lead to death.

While various methods and devices are available to treat a blockage or obstruction through removal of the obstructing clot, these devices can be traumatic to the blood vessel due to stiffness and pressure exerted on the lining of the vessel during clot engagement and removal. In addition, they usually do not sufficiently capture and retain the particulate matters from the obstruction. In particular, these methods usually cause fragmentation of the clot either during device engagement of the clot or due to the friction between the not fully encapsulated clot with the wall of the vessels or the flowing blood during the removal from the body. This fragmentation of the clot can lead to migrating of clot fragments with the blood flow either to the same treated blood vessels and its branches distal to the original obstruction site or to another unaffected area of the vascular system in the branching circulation at or proximal to the site of the obstruction where they can get lodged again and causes further obstruction. There remain a need for new devices to safely remove the obstructing clot fully encapsulated and shielded from the friction force with the blood vessel wall and the flowing blood to prevent excessive fragmentation and distal migration

BRIEF SUMMARY OF THE INVENTION

Embodiments of the present invention provides a minimally invasive endovascular device for treating a blocked or obstructed biological lumen, such as a blood vessel fully or partially obstructed by deposits of biological matters in or non-biological matters. Certain embodiments of the present invention comprise two capture members that are configured to be placed on either side of the obstruction and enclose around the obstruction for removal. Embodiments of the present invention also provide methods for implementing an endovascular device according to aspects of the present invention.

According to one aspect of the present invention, a device to remove an obstruction in a lumen is described. The device comprises a first capture member, a second capture member, where each capture member comprises an open end and a tapered end. The open end is defined by a frame component coupled to a body component, the body component extending between the open end and the tapered end. The device further comprises a first guide member coupled to the first capture member at the open end, where at least a portion of the body component is attached to the first guide member, and a second guide member coupled to the second capture member at the open, where at least a portion of the body component is attached to the second guide member, where the first capture member and the second capture member are slidably coupled to each other, the slidable coupling comprises the first guide member disposed in the second guide member.

In one embodiment, the device further comprises a radiopaque marker. In another embodiment, the frame component is configured to fit within a catheter for delivery to the obstruction and to expand to define the open end when released from the catheter, the catheter having a radius smaller than a radius of the open end. In one embodiment, the frame component comprises a self-expanding material configured to have an original configuration and a deformed configuration; where the self-expanding material is configured to change from the deformed configuration to the original configuration at least by exposure to an activating condition. In another embodiment, the deformed configuration allows the device to fit within the catheter.

In one embodiment, the body component is attached to the respective guide member substantially along the length of the body component. In another embodiment, at least one capture member further comprises a support arm coupled to the respective guide member and the respective frame component. In one embodiment, the support arm comprises a first end and a second end, where the first end is coupled to the respective frame component and the second end is coupled to the respective guide member. In another embodiment, the second end is attached to the respective guide member. In another embodiment, the respective guide member further comprises a fastening member slidably coupled to the respective guide member and where the second end is attached to the fastening member.

In one embodiment, the body component is fluid impermeable. In another embodiment, the body component comprises a woven material of at least one of the following: a polymer, a methal, and any combination thereof. In another embodiment, the body component covers at least a portion of a surface of the frame component to which the body component is coupled. In another embodiment, at least one guide member is adapted to provide a suctioning force.

In one embodiment, the diameter of one frame component is smaller than the diameter of the other frame component.

In another embodiment, at least one frame component comprises an inflatable member. In another embodiment, the device further comprises an inflatable member disposed near at least one frame component.

In one embodiment, at least one guide member comprises a body with a channel disposed therein, the body having at least one aperture positioned near an end near the respective capture member. In one embodiment, the guide member is used to provide a suctioning force. In one embodiment, the guide member is used to deliver a therapeutic substance to the obstruction. In another embodiment, the coupling between at least one guide member and the respective frame member comprises the at least one guide member attached to an outer surface of the respective frame member.

According to another aspect of the present invention, there is provided a method for removing an obstruction in a lumen. The method comprises the steps of delivering an endovascular device to the location of the obstruction in a patient using a catheter, where the device comprises a first capture member and a second capture member, where each capture member comprises an open end and a tapered end, where the open end comprises a frame component coupled to a body component, the body component extending between the open end and the tapered end. The device further comprises a first guide member coupled to the first capture member at the open end and along at least a portion of the body component, and a second guide member coupled to the second capture member at the open end and along at least a portion of the body component, where the first capture member and the second capture member are slidably coupled to each other, the slidable coupling comprises the first guide member disposed in the second guide member. The method further comprises the steps of positioning a distal end of the catheter distal to the obstruction, withdrawing the catheter to release the first capture member distal to the obstruction; positioning the distal end of the catheter proximal to the obstruction; withdrawing the catheter to release the second capture member proximal to the obstruction; enclosing the obstruction with the capture members by manipulating at least one of the first guide member or the second guide member to unite the capture members; and removing the captured obstruction by removing the united capture members from the lumen.

In one embodiment, the method further comprises the step of providing a suctioning force through at least one guide member. In another embodiment, the method further comprises the step of repeatedly moving at least one frame member against the obstruction. In another embodiment, the method further comprises the step of delivering a therapeutic substance to the obstruction. In one embodiment, the delivering is achieved at least through one of the guide members, the guide member comprising a body with a channel disposed therein, the body having at least one aperture positioned near an end near the respective capture member.

In one embodiment, the enclosing step comprises manipulating the first guide member to engage a surface of the first capture member with a surface of the obstruction while the second guide member is maintained stationary. In another embodiment, the enclosing step comprises manipulating the second guide member to engage a surface of the second capture member with a surface of the obstruction while the first guide member is maintained stationary. In another embodiment, the enclosing step comprises manipulating both the first and second guide members to engage a surface of both capture members with a surface of the obstruction.

The foregoing has outlined rather broadly the features and technical advantages of the embodiments of the present disclosure in order that the detailed description of these embodiments that follows may be better understood. Additional features and advantages of the embodiments of the present disclosure will be described hereinafter which form the subject of the claims of the present disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the present disclosure as set forth in the appended claims. The novel features which are believed to be characteristic of the present disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the embodiments of the present invention, reference is now made to the following descriptions taken in conjunction with the accompanying drawing, in which:

FIGS. 1A-1C illustrate side perspective views of certain exemplary stages in an exemplary embodiment of a procedure for using a first embodiment of the endovascular device according to certain aspects of the present invention.

FIGS. 4A-4D illustrate side perspective views of certain exemplary stages in an exemplary embodiment of a procedure for using a second embodiment of the endovascular device according to certain aspects of the present invention;

FIG. 5 illustrates a perspective side view of the second embodiment of the endovascular device according to certain aspects of the present invention in a closed configuration entering a catheter;

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. Also, for simplification purposes, there may be only one exemplary instance, rather than all, is labeled. It should be understood, of course, that this disclosure is not limited to the particular embodiments illustrated herein.

DETAILED DESCRIPTION OF THE INVENTION

Embodiments of the present invention provide for minimally invasive removal of obstructing material, such as a clot or embolism, disposed in a patient's (human or otherwise) vascular system. Certain embodiments of the present invention are particularly applicable for extraction of material in small, tortuous and highly branching segments of the neurovascular system. In a general embodiment, the endovascular device of the present invention includes two opposing capture members that are slidably coupled to each other. Each capture member preferably comprises an open end and a tapered end, where the open end of each capture member faces one another. In one embodiment, the endovascular device can be delivered to the site of the material deposit using a catheter. The capture members can be placed on each side of the material deposit with the open ends facing the material deposit. In one embodiment, the open end of each capture member is supported by a frame component. In another embodiment, the capture members are slidably coupled to one another to allow the capture members to move in the distal and proximal directions to facilitate in dislodging the clot from the arterial wall. In a preferred embodiment, the majority of the material deposit is moved into the capture members at the site of lodging when the capture members encloses the clot as they progress toward one another. In one closed configuration, the open end of the capture members meet one another to form an enclosure to capture and retain the material deposit contained therein. The capture members can be withdrawn in this closed configuration and/or be pulled into a catheter, thereby removing the material deposit. Embodiments of the present invention provide for clot removal without excessive force or compression of the clot, thereby minimizing fragmentation of the clot or squeezing of the clot into side branches that may exist at the site of obstruction, which can lead to further damage.

Figure 2:
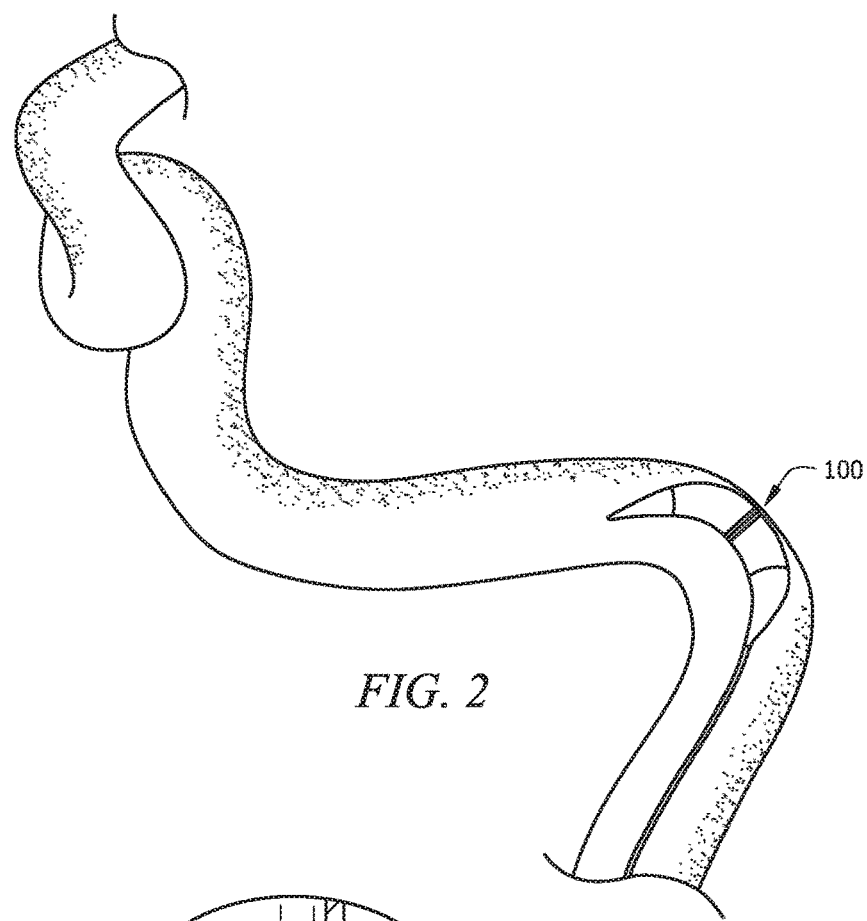
FIG. 2 illustrates a perspective view of the first embodiment of the endovascular device according to certain aspects of the present invention in a closed configuration traveling through a blood vessel.
Figure 3:
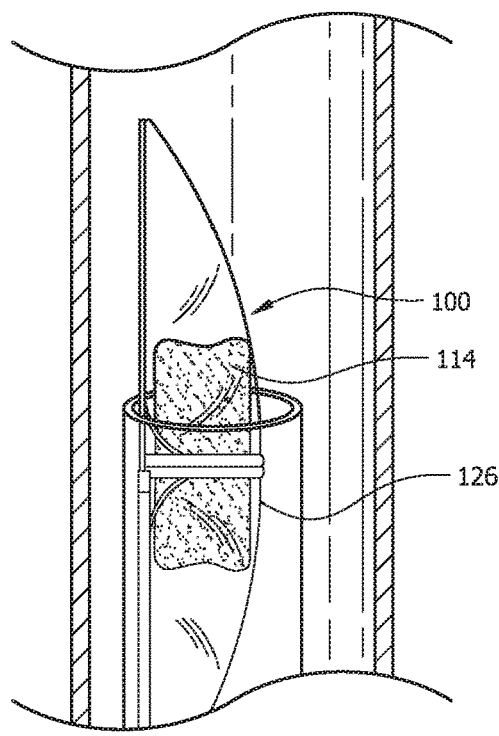
FIG. 3 illustrates a perspective side view of the first embodiment of the endovascular device according to certain aspects of the present invention in a closed configuration entering a catheter.

FIGS. 1-3 show certain specific embodiments according to the aspects of the present invention. FIGS. 1A-1C show capture members 102 and 104 of endovascular device 100 in a fully expanded configuration. Capture member 102 is the proximal capture member while capture member 104 is the distal member with respect to obstruction 114. In one embodiment, capture members 102 and 104 substantially resemble each other, each comprising open end 106, tapered end 108, and body component 110 extending between open end 106 and tapered end 108. Open end 106 preferably comprises open end support member or frame component 112 defining the shape and size of open end 106 when capture members 102 and 104 are expanded. Frame component 112 preferably has a circular shape that matches the shape of the target blood vessel. In other embodiments, however, frame component 112 can have any shape in the expanded configuration desired, such as circular, oval, rectangular or any other regular or irregular shapes that may be suitable to the particular application.

In one embodiment, frame component 112 comprises a self-expanding material including, but not limited to, a metal, an alloy, a composite, a polymer, and the like. In one non-limiting example, frame component 112 comprises nitinol, stainless steel, cobalt chromium, platinum, titanium, plastic, or any combination thereof. In another embodiment, frame component 112 comprises a superelastic and/or self-expanding material with properties that allow it to have a deformed shape under one condition and to recover its original shape prior to deformation, which can also be referred to as an expanded configuration. A non-limiting example is a memory-shaped heated alloy such as nitinol, or nickel titanium, which is a metal alloy of nickel and titanium. Nitinol alloys exhibit two closely related and unique properties: shape memory and superelasticity. Shape memory refers to the ability of nitinol to undergo deformation at one temperature, then recover its original, un-deformed shape upon heating above its "transformation temperature." That is, nitinol alloy has a biased expanded condition and may be compressed into a collapsed or deformed condition before use. During use, it may be exposed to temperature above the transformation threshold, thereby causing it to revert back to its un-deformed and/or original shape. Frame component 112 can also comprise any flexible and/or elastic material that allows frame component 112 to be compressed, or deformed by a radial force, to fit into a catheter, such as catheter 122, without sustaining any damage and revert back to its original shape once released from the catheter.

Figure 8A:
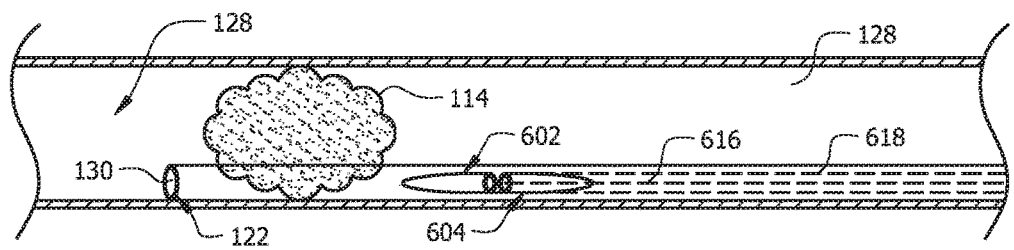
FIGS. 8A-8F are side perspective views of certain exemplary stages in an exemplary embodiment of a procedure for using the endovascular device shown in FIG. 7 according to certain aspects of the present invention.
Figure 8B:
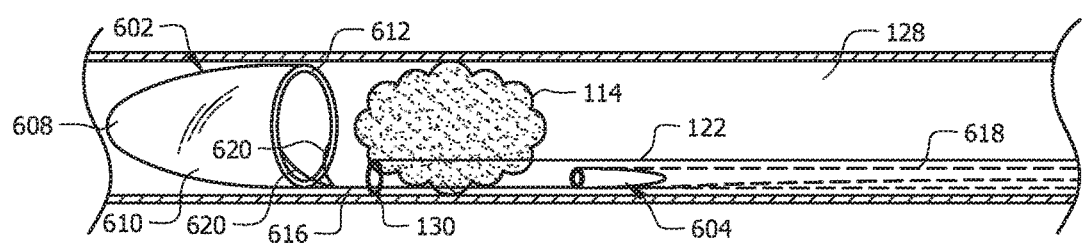

In one embodiment, such as that shown in FIGS. 8A-8B, frame component 112 has a deformed or compressed shape with a smaller diameter than the un-deformed, expanded shape shown in FIGS. 1A-1C. In one embodiment, the thickness of frame component 112 is in a range between about 10 microns to 500 microns. In a preferred embodiment, the thickness of frame component 112 is in a range between about 80 microns to about 120 microns. In another preferred embodiment, the thickness of frame component 112 is in a range between about 95 microns to about 105 microns.

Referring to FIGS. 1A-1C, in a preferred embodiment, the diameter across frame component 112 in an expanded configuration, and thus open end 106, is configured to substantially match the diameter of the particular lumen or blood vessel of interest in which the obstruction, e.g., clot 114, is disposed. In such an expanded configuration, frame component 112 preferably contacts the inner wall of the target blood vessel gently, e.g., without exerting significant force that can damage the blood vessel. This allows at least one capture member 102 or 104 to extend across the interior, or lumen, of the blood vessel where effectively most or all obstructing materials are directed through the respective extended capture member 102 or 104. In one embodiment, the diameter of open end 106 is in a range of about 1.5 mm to about 6 mm, and preferably in a range of about 2 mm to about 4.5 mm. In another preferred embodiment, the diameter of open end 106 is between about 2.5 mm and about 3 mm. It is understood that other embodiments can include capture members 102 and 104 of different sizes and configurations. For instance, in one embodiment, one capture member has an open end with a smaller diameter than the other capture member so that one can be inserted into the other, providing an overlapping area. In another embodiment, endovascular device 100 is provided in various sizes and configuration depending on the location of the material deposit to be removed.

Referring to FIGS. 1A-1C, in a preferred embodiment, open end 106 further comprises one end of body component 110 coupled to frame component 112. In such an embodiment, when the respective capture member, 102 or 104, is released from catheter 112, it expands into the configuration shown in FIGS. 1A-1C. In one embodiment, this is achieved with the expansion of frame component 112, which opens body component 110 for material to enter. Body component 110 is preferably formed of any material which is flexible and compatible with bodily tissues and fluids such as blood. In a preferred embodiment, body component 110 is devoid of any fenestration, i.e., the material of body component 110 is impermeable to fluid. Non-limiting examples of suitable materials include polymeric film or fabric-like materials, such as, but not limited to, polyurethane, polyolefin, polyester, plastic, silicone polymers, and any combination thereof. In one embodiment, the material of body component 110 has properties, such as being soft and flexible, that are configured to minimize friction and/or pressure placed on the wall upon contact of the capture members with the lining of the vessel during implementation of device 100. In an alternative embodiment, tapered end 108 can further include at least one fenestration of sufficient size to allow fluids to flow through body component 110 while retaining the captured material deposit. In one embodiment, the material of body component 110 can comprise a material with self-expanding properties as described above, providing it a biased shape in the expanded configuration that allows body component 110 to remain open as it extends away from frame component 112.

Body component 110 can be coupled to frame component 112 in any suitable manner. In one embodiment, body component 110 can be attached to frame component at or near the inner diameter or outer diameter of frame component 112. In another embodiment, body component 110 surrounds at least a portion of frame component 112. In such an embodiment, the material of body component 110 contacts the inner wall of the lumen in the expanded configuration instead of frame component 112, which can help protect the inner wall from potential damage or injury resulting from contact with frame component 112 itself.

Alternatively, expansion of one capture member, 102 or 104, when released from a catheter can be achieved through mechanical means known to those skilled in the art. In one embodiment, frame component 112 comprises an inflatable member comprising an enclosed fillable volume, such as a balloon, that expands when the member is filled with a fluid. In this embodiment, the inflatable member has the shape of frame component 112 as shown, e.g., annular, and body component 110 is coupled to the inflatable frame component. When released from catheter 122, frame component 112 can be expanded by filling the interior of the inflatable member with fluid using methods known to those skilled in the art. The diameter of the inflatable member, and thus, open end 106, can be adjusted based on the amount of fluid provided to the inflatable member. In another embodiment, instead of forming frame component 112 with an inflatable member, frame component 112 is expanded through the expansion of an inflatable member. The inflatable member has a shape that corresponds to the shape of frame component 112 where it can be placed at or near the respective open end 106 so that the radial expansion of the inflatable member pushes against the respective frame component 112 to expand it. Once the respective frame component is expanded, the inflated members can be deflated and removed as appropriate. It is understood that other ways of using an inflatable known to one of ordinary skill in the art can also be used. Other ways can include the addition of self-expanding wire(s) coupled to the inner wall of at least one capture member in circular pattern, longitudinal pattern, helical pattern, or any combination thereof.

Referring to FIG. 1C, when capture members 102, 104 unite to form one capture enclosure, the length of the capture enclosure preferably is longer than the length of the target obstruction, e.g., clot 114. In one embodiment, the total length of both capture members united is between about 5 mm and about 30 mm. In a preferred embodiment, the total length of both capture members united is between about 8 mm and about 20. In another preferred embodiment, the total length of both capture members united is between about 10 mm and 12 mm. In yet another preferred embodiment, the total length of both capture members united is about 10 mm.

Referring to FIGS. 1A-1C, capture members 102 and 104 are slidably coupled to one another with the open ends facing each other, allowing them to be moved apart or unite to form one enclosure. In a preferred embodiment, distal capture member 104 is coupled to distal guide member 116, and proximal capture member 102 is coupled to proximal guide member 118. Distal guide member 116 is preferably disposed in proximal guide member 118. In this configuration, the relative position of capture members 102 and 104 can be adjusted in various manners. In one embodiment, a user can hold proximal guide member 118 constant, thereby keeping proximal capture member 102 in one position, while pushing or pulling distal guide member 116 to adjust the position of distal capture member 104. In another embodiment, the user can hold distal guide member 116 constant, thereby keeping distal capture member 104 in one position, while pushing or pulling proximal guide member 118 to adjust the position of proximal capture member 102. In yet another embodiment, both guide members 116 and 118 can be adjusted at the same time to achieve the desired positions of capture members 102 and 104 with respect to each other. Once capture members 102, 104 are in a desired position, that position can be maintained by attaching guide members 116, 118 together, thereby stabilizing endovascular device 100. In one embodiment, distal guide member 116 comprises a solid body, such as a wire; alternative, it can comprise a body with an interior channel, such as a tube. In a preferred embodiment, proximal guide member 118 comprises a tube. In another embodiment, proximal guide member 118 is configured with suction capabilities to assist with bringing clot 114 into capture member 102 and/or 104. In yet another embodiment, both guide members 116, 118 comprise a body with a channel disposed therethrough having at least one aperture on the body, so guide members 116,118 can be used to provide a suctioning force. Alternatively, or in addition to, the at least one aperture on the body of such guide members in such an embodiment is preferably located near (e.g., at or proximal) clot 114 so that these guide members can also be used to deliver desired substances locally to the site of clot 114. Non-limiting examples of substances that can be delivered include medication configured to facilitate dislodging and removal of clot 114, such as clot dissolving medication that softens and shrinks the clot.

The body of either guide member 116, 118 preferably has a length sufficient to extend through the vascular system of a patient to reach the target accumulation and place endovascular device 100 in the desired deployment location. In one embodiment, either guide member 116, 118 has a length of between about 50 cm and about 250 cm, more preferably a length of about 125 cm and about 175 cm. The diameter of either guide member 116, 118 may be constant or may vary along the length of the respective guide member 116, 118. For example, the diameter of one guide member toward the proximal end away from the user may be between about 0.2 mm and about 1 mm, and preferably about 0.3 mm and about 0.4 mm, while the diameter near the distal end near the clot may be between about 0.05 mm and about 1 mm, and more preferably about 0.1 mm and about 0.2 mm. Accordingly, the diameter of either guide member 116, 118 may taper from the proximal end to the distal end.

Referring to FIGS. 1A-1C, distal capture member 104 is preferably coupled to distal guide member 116 via frame component 112. In a preferred embodiment, frame component 112 is preferably coupled to distal guide member 116 at an angle of about 90 degrees. In one embodiment, the angle between guide member 116 and frame component 112 can be further supported by at least one additional support arm 120, preferably extending between distal guide member 116 and frame component 112. In a preferred embodiment, one end of support arm 120 is coupled to the respective frame component 112 while the other end of support arm 120a is coupled to guide member 116. In another embodiment, one end of support arm 120 is coupled to the respective frame component 112 and the other end is coupled to a fastening component (not shown) slidably coupled to guide member 116, allowing the coupling angle of the respective frame component 112 to be adjusted. In one embodiment, one end of support arm 120 is coupled to distal guide member 116 in a manner that allows it to extend in the proximal direction when capture member 102 is released from catheter 122. In one embodiment, capture member 102 has more than one support arms 120. In another preferred embodiment, body component 110 is attached to distal guide member 116 along at least a portion of the length of body component 110 or only tapered end 108 is coupled to distal guide member 116. In yet another embodiment, body component 110 is coupled to distal guide member 116 from open end 106 to tapered end 108, along the length of body component 110.

In a preferred embodiment, each guide member 116, 118 has one attachment site to the outer circumference of its respective frame, thereby leaving substantially all of the respective frame component 112 and open end 106 available for engagement with clot 114. Such a configuration allows for easier transmission of the captured clot inside device 100 through the tortuous paths with minimal interference from guide members 116, 118 or their attachment to frame components 112. Further, this configuration allows the segment of distal guide member 104 to act like a railing upon which clot 114 can move inside capture members 102, 104 when distal capture member 104 is held constant and proximal capture member 102 is pushed.

Proximal capture member 102 is preferably coupled to proximal guide member 118 in a similar manner. In a preferred embodiment, frame component 112 of proximal capture member 102 is preferably coupled to proximal guide member 118 at an angle of about 90 degrees. In one embodiment, the angle between guide member 118 and capture member 104 can be further supported by at least one additional support arm 120a, preferably extending between proximal guide member 118 and frame component 112 of proximal capture member 102. In a preferred embodiment, one end of support arm 120a is coupled to frame component 112 while the other end of support arm 120a is coupled to guide member 118. In another embodiment, one end of support arm 120a is coupled to the respective frame component 112 and the other end is coupled to a fastening component (not shown) slidably coupled to guide member 118, allowing the coupling angle of the respective frame component 112 to be adjusted. In one embodiment, one end of support arm 120a is coupled to proximal guide member 118 in a manner that allows it to extend in the distal direction when proximal capture member 102 is released from catheter 122. In another embodiment, capture member 104 has more than one support arms 120a. In another embodiment, body component 110 is coupled to proximal guide member 118 along at least a portion of the length of body component 110 or only tapered end 108 is coupled to proximal guide member 118. In yet another embodiment, body component 110 is attached to proximal guide member 118 from open end 106 to tapered end 108, along the length of body component 110.

In a preferred embodiment, body component 110 of capture members 102 and 104 are configured to fully encapsulate clot 114 and prevent migration of clot 114, thereby reducing the risk of clot 114 from unintentionally ending up at another location in the patient's body. In one embodiment, this is achieved by forming body component 110 of suitable materials do not have any fenestration.

In a preferred embodiment, endovascular device 100 includes at least one radiopaque portion to facilitate visualization using, for example, one or more of fluoroscopy, computer tomography (CT) fluoroscopy, or the like. The radiopaque portion can be a component of endovascular device 100. In one embodiment, at least one frame component 112 comprises a radiopaque material. Non-limiting examples of a radiopaque material include platinum or tantalum DFT Nitinol. Referring to FIG. 2, in another embodiment, a separate radiopaque marker is provided, such as radiopaque component 124 coupled at the junction where frame component 112 is coupled to the respective guide member, e.g., distal guide member 116. Endovascular device 100 can have one or more than one radiopaque marker coupled at various positions. For instance, each capture member 102, 104 can have its own radiopaque component 124.

Referring to FIGS. 2-3, once all or substantially all of clot 114 is captured in the enclosure formed by capture members 102, 104, clot 114 can be removed by holding guide members 116, 118 together so they can remain united with one another as a unit and be withdrawn together with clot 114 contained therein. Referring to FIG. 2, capture members 102, 104 can be pulled through a stretch of blood vessels as a unit containing clot 114 before device 100 enters catheter 126, as shown in FIG. 4, for removal from the patient's body. In the embodiment shown, catheter 126 has a diameter that is larger than the diameter of frame components 112.

FIGS. 4A-4D and 5 illustrate another embodiment of the endovascular device of the present invention, endovascular device 400. In a preferred embodiment, endovascular device 400 is similar to endovascular device 100, except open end 406 of distal capture member 404 is smaller than open end 406 of proximal capture member 402. As shown, in one embodiment, the outer diameter of frame component 412 of distal capture member 404 is smaller than the outer diameter of frame component 412 of the proximal capture member 402. This configuration can help to reduce any opening or gap that can form between both frame components 412 when they unite with one another. Other features discussed herein with respect to endovascular device 100, such as dimensions, materials, strand density, strand diameter, shape, position with respect to the blood vessel interior wall, coupling of guide members, radiopaque marker, etc., are also applicable to endovascular device 400, and thus need not be repeated.

Referring to FIG. 5, once all or substantially all of clot 414 is captured in the enclosure formed by capture members 402, 404, and clot 414 can be removed by holding guide members 416, 418 together so they can remain united with one another as a unit and be withdrawn together with clot 414 contained therein. The united capture members 402, 404, along with clot 414 can be pulled into catheter 424 for removal.

Figure 6A:
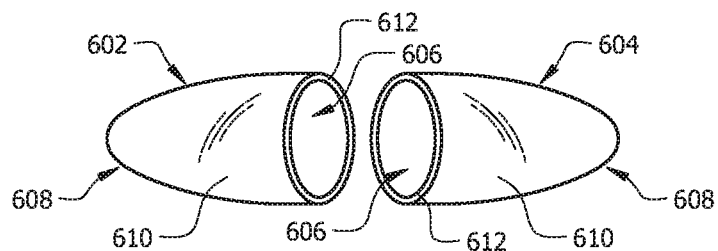
FIGS. 6A and 6B illustrate side perspective views of a third embodiment of capture members of the endovascular device according to certain aspects of the present invention.
Figure 6B:
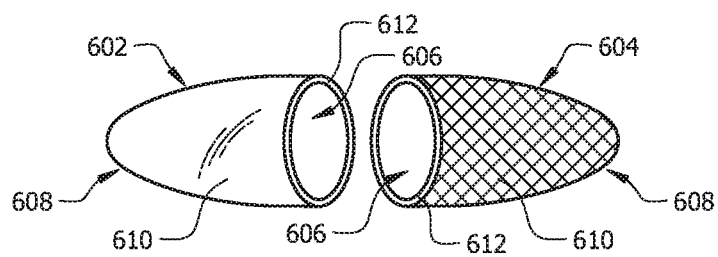
Figure 7:
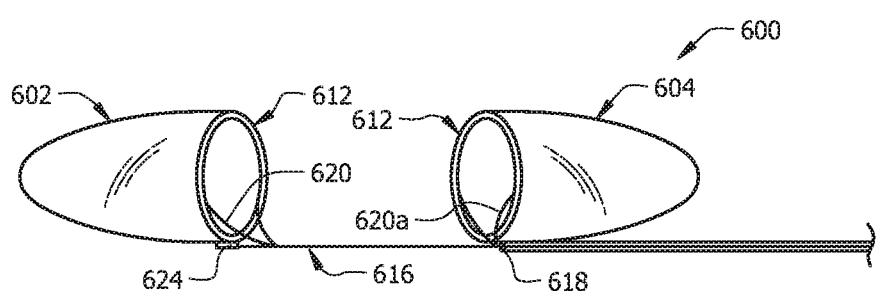
FIG. 7 illustrates a side perspective view of the capture members of FIG. 6A coupled to one another.

FIGS. 6A-6B, 7, and 8A-8F illustrate another embodiment of the endovascular device of the present invention, endovascular device 600. In a preferred embodiment, endovascular device 600 is similar to endovascular device 100, except for several features. In the embodiment shown in FIGS. 6A-6B, 7, and 8A-8F, tapered end 608 of capture members 602, 604 are not coupled to the respective guide members 616, 618. Referring to FIG. 6B, in another embodiment, body component 610 comprises polymeric net-like materials having a plurality of fenestrations throughout the material, such as, but not limited to, a woven mesh of polymeric material, metal, and/or other superelastic, self-expanding, and/or memory shape alloy such as nitinol. In certain embodiments, the woven mesh can comprise a combination of polymers, metals, and/or metal alloys. Referring to FIG. 7, one end of support arm 620 is coupled to distal guide member 616 in a manner that allows it to extend in the distal direction when capture member 602 is released from catheter 122. Likewise, in the embodiment shown, one end of support arm 620a is coupled to proximal guide member 618 in a manner that allows it to extend in the proximal direction when proximal capture member 604 is released from catheter 122. Endovascular device 600 can have any number of support arms 620, 620a. Further, support arms 620, 620a can be slidably coupled to the respective guide members 616, 618 as described above with respect to support arms 120, 120a. Other features discussed herein with respect to endovascular device 100, such as dimensions, materials, strand density, strand diameter, shape, position with respect to the blood vessel interior wall, coupling of guide members, radiopaque marker, etc., are also applicable to endovascular device 600, and thus need not be repeated.

According to another aspect of the present disclosure, there is a method of removing one or more material deposits in a lumen, such as a clot in a blood vessel, using embodiments of the endovascular device of the present invention, such as device 100, device 400, or device 600. While the disclosure may refer to numerical components of only one of device 100, 400, or 600, it is understood that the discussion is applicable to other unmentioned device and its components. In one embodiment, an endovascular device according to aspects of the present invention, e.g., device 100, 400, or 600, configured to match the conditions, e.g., dimensions and shape, of the material deposit to be removed and the corresponding lumen conditions is selected.

Referring to FIG. 8A, catheter 122 is provided to deliver endovascular device 100, 400, or 600 to the site of the obstruction, or clot 114, in lumen 128. Catheter 122 can be referred to as a delivery catheter. In one embodiment, catheter 122 is a fluoroscopy microcatheter so visualization methods known to those skilled in the art, such as fluoroscopy, can be used to assist in delivering catheter 122 to the desired location. Catheter 122 is inserted into a patient's vessel and moved to clot 114 using means known to those skilled in the art, such as using another catheter, guide catheter 126, as shown in FIGS. 1A-1C. In such an embodiment, catheter 122 containing the endovascular device is advanced through the patient's body in guide catheter 126. As catheter 122 approaches clot 114, it naturally gravitates near the inner wall of lumen 128. In a preferred embodiment, tip portion 130 of catheter 122 is moved distally through clot 114 to place tip portion 130 at a position distal to clot 114. In a preferred embodiment, catheter 122 navigates to clot 114 without endovascular device 100, 400, or 600 therein; however, catheter 122 with endovascular device 100, 400, or 600 can travel to clot 114 together. After catheter 122 is at a desired position, endovascular device 100, 400, or 600 is inserted into the lumen of catheter 122 in a compressed or collapsed configuration and can be moved through catheter 122 to arrive at clot 114. In a preferred embodiment, endovascular device 100, 400, or 600 comprises flexible material that allows it to conform to catheter 122 as it makes its way through potentially tortuous paths without sustaining damage.

In a preferred embodiment, when the distal end of endovascular device 100, 400, or 600 approaches tip portion 130, device 100, 400, or 600 is stabilized or steadied by manipulating the respective guide members (e.g., 116, 118) to place the respective capture members (e.g., 102, 104) in the desired positions and holding the guide members (e.g., 116, 118) together in place to maintain those positions. Referring to FIGS. 4A-4B and 8B, catheter 122 is then slowly withdrawn to release or unsheathe the distal capture member (e.g., 102, 402, or 602) at a position distal to clot 114. When released, the distal capture member (e.g., 102, 402, or 602) expands to gently touch the inner lining of the vessel wall to open the respective body member (e.g., 110, 410, or 610) to receive clot material. Non-limiting exemplary manners of expansion, such as through self-expanding material or mechanical expansion, including using inflatable members, are described above. In a preferred embodiment, the expansion of the distal capture member (e.g., 102, 402, or 602) is preferably achieved with the expansion of its frame component (e.g., 112 412, or 612), and/or body component (e.g., 110, 410, or 610) to the original or expanded configuration. The distal guide member (e.g., 116, 416, or 616) is preferably stabilized, steadied, or held in place to maintain the distal capture member (e.g., 102, 402, or 602) in the desired position distal to clot 114. Catheter 122 and the proximal guide wire (e.g., 118, 418, or 618) are then preferably held together so their movement are coupled to each other. Catheter 122 and the proximal guide wire (e.g., 118, 418, or 618) are then preferably moved in the proximal position together as a unit to place the proximal capture member (e.g., 104, 404, or 604) at a location proximal to clot 114. Once the proximal capture member (e.g., 104, 404, or 604) is in a desired location, the proximal guide member (e.g., 118, 418, or 618) is then preferably coupled or held with the distal guide member (e.g., 116, 416, or 616) to stabilize both capture members, maintaining them at the respective positions distally and proximally to clot 114.

Figure 8C:
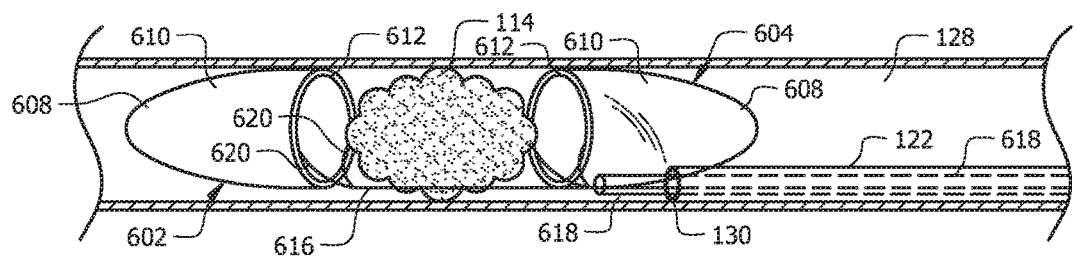

Next, referring to FIGS. 1A and 8C, catheter 122 is further withdrawn to unsheathe or release the proximal capture member (e.g., 104, 404, or 604), which expands in a similar manner as the distal capture member (e.g., 102, 402, or 602) as described above when released from the lumen of catheter 122, to a position proximal to clot 114. In one embodiment, the coupling angle between the frame component (e.g., 112, 412, or 612) and the respective guide member (e.g., 116, 118; 416, 418; or 616, 618) can be increased and decreased by adjusting the position of the respective supporting arm (e.g., 120, 120a; or 420, 420a; or 620, 620a). This can be achieved by applying force to the fastening member slidably coupled to the respective guide member as described above in the desired direction, i.e., proximally or distally.

Figure 8D:
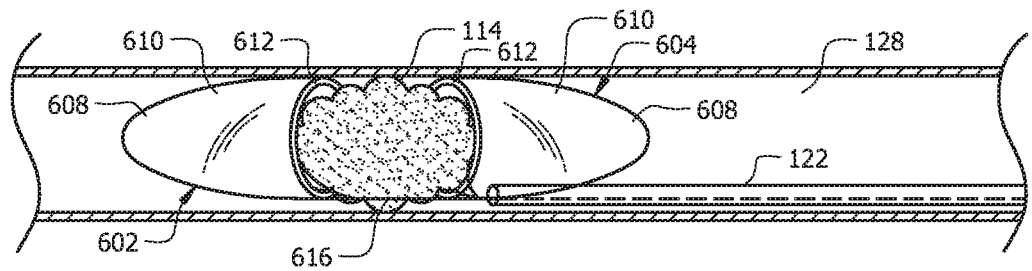

Referring to FIGS. 1B, 4C, and 8D, both guide members (e.g., 116, 118; 416, 418; or 616, 618) are manipulated to bring the capture members (e.g. 102, 104; 402, 404; or 602, 604) together. As shown in FIGS. 1B, 4C, and 8D, frame components (e.g., 112, 412, or 612) of the capture members begin to engage the outer surface of the respective side of clot 114. In one embodiment, the dislodging of clot 114 can be further aided by repetitively moving at least one capture member (e.g. 102, 104; 402, 404; or 602, 604) against clot 114. This can be done by repetitive moving of the respective guide member itself and/or repetitive moving of the fastening member slidably coupled to that guide member. The effect is to gently separate clot 114 from the wall of lumen 128 before pulling the capture members over separated clot 114, which allows for easier encapsulation of clot 114.

In one embodiment, proximal capture member (e.g., 104, 404, or 604) remains in one position while the distal capture member (e.g., 102, 402, or 602) is moved via manipulation of the distal guide member (e.g., 116, 416, or 616) to engage the distal end of clot 114 and bring clot 114 into both capture members (e.g. 102, 104; 402, 404; or 602, 604). The distal guide member (e.g., 116, 416, or 616) is preferably continued to be withdrawn or pulled until the frame component (e.g., 112, 412, or 612) of the distal capture member (e.g., 102, 402, or 602) unites or engages with the frame component (e.g., 112, 412, or 612) of the proximal capture member (e.g., 102, 402, or 602). Alternatively, for embodiments using frame components (e.g., 112, 412, or 612) of different diameters, the distal guide member (e.g., 116, 416, or 616) is preferably continued to be withdrawn or pulled until the capture members (e.g. 102, 104; 402, 404; or 602, 604) join one another. In another embodiment, the distal capture member (e.g., 102, 402, or 602) is kept in place while the proximal capture member (e.g., 104, 404, or 604) is pushed in the distal direction toward the distal capture member (e.g., 102, 402, or 602) to engage the proximal end of clot 114 and bring clot 114 into both capture members (e.g. 102, 104; 402, 404; or 602, 604) through manipulation of the proximal guide member (e.g., 118, 418, or 618). In yet another embodiment, both capture members (e.g. 102, 104; 402, 404; or 602, 604) can be moved toward one another, through manipulations of both guide members (e.g., 116, 118; 416, 418; or 616, 618) to engage the respective side of clot 114. If equipped with suction capabilities, suctioning force can be applied when desired to further help direct clot 114 into either capture member (e.g. 102, 104; 402, 404; or 602, 604).

Figure 8E:
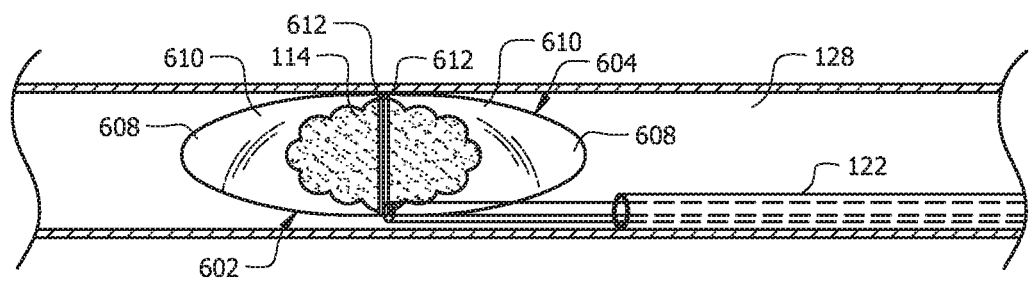
Figure 8F:
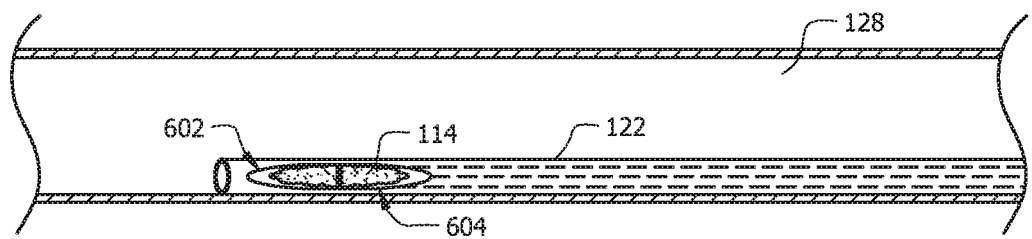
Figure 9:
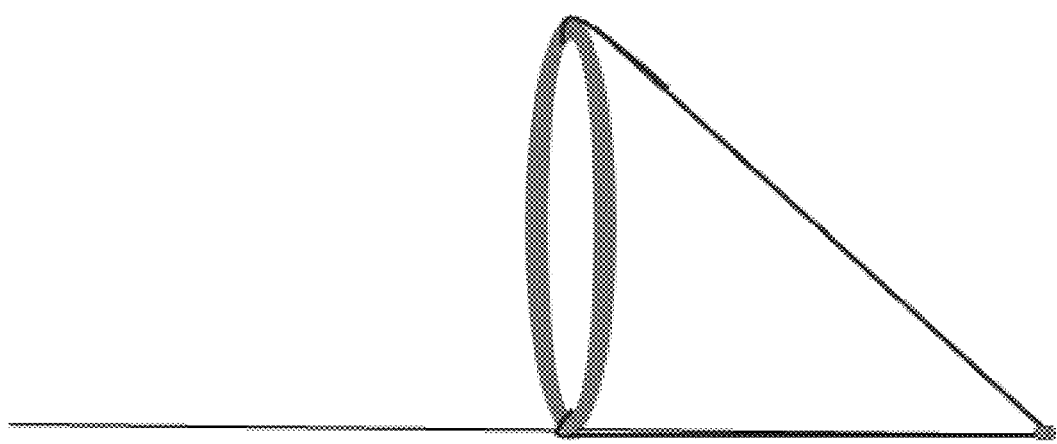
FIG. 9 depicts a capture member comprising an open end and a tapered end, with the open end comprising a frame component coupled to the body component.

Referring to FIGS. 1C, 4D, and 8E, once all or substantially all of clot 114 is captured in the enclosure formed by capture members (e.g. 102, 104; 402, 404; or 602, 604), clot 114 can be removed by holding guide members (e.g., 116, 118; 416, 418; or 616, 618) together so they can remain united with one another as a unit and be withdrawn together with clot 114 contained therein. Referring to FIG. 2, capture members (e.g. 102, 104; 402, 404; or 602, 604) can be pulled through a stretch of blood vessels as a unit containing clot 114 before device 100, 400, or 600 enters catheter 126, as shown in FIGS. 3 and 5, for removal from the patient's body. As shown in FIG. 2, the flexibility of certain embodiments of the components according to certain aspects of the invention allow device 100, 400, or 600 to conform to tortuous paths in a patient's body without inflicting additional damage as it is pulled out of the patient. Alternatively or in addition to, referring to FIG. 8F, device 100, 400, or 600, along with clot 114, can be withdrawn into catheter 122 for removal, where catheter 122 has a diameter smaller than the diameter of frame component 112 in the expanded configuration, thereby compressing clot 114.

As described, certain embodiments of the present invention provide for an endovascular device containing less overall metal material, making the device more flexible with smaller profile, which is particularly applicable to ease of navigation in small and torturous brain circulation. Certain embodiments with less metallic material also provide less trauma to the lining of the small and fragile brain blood vessels during insertion and removal. The shape and size of the capture members of certain embodiments allow for better entrapment of the obstruction without significant compression of deformation which mean less fragmentation or pushing into normal side branch. In certain embodiments, the coupling of the frame component to the respective guide member leaves the open end of the capture member unobstructed, giving more space for the clot material to enter the capture member.

Although the embodiments of the present disclosure and their advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A device to remove an obstruction in a lumen comprising:
   a first capture member
   a second capture member;
   each capture member comprises an open end and a tapered end, wherein said open end comprises a frame component coupled to a body component, said body component extending between said open end and said tapered end;
   wherein a first frame component is a different diameter than a second frame component;
   a first guide member directly connected to said first capture member at an open end and a tapered end of a first body component;
   a second guide member directly connected to said second capture member at an open end and a tapered end of a second body component; and
   wherein said first capture member and said second capture member are slidably coupled to each other, said slidable coupling comprises said first guide member disposed in said second guide member,
   wherein at least one capture member further comprises a support arm coupled to a respective guide member and a respective frame component,
   wherein said support arm comprises a first end and a second end, wherein the first end is coupled to a respective frame component and the second end is coupled to a respective guide member, wherein a respective guide member further comprises a fastening member slidably coupled to said respective guide member and wherein the second end is attached to said fastening member.

2. The device of claim 1 further comprising:
   a radiopaque marker.

3. The device of claim 1 wherein each of the first and second frame components are configured to fit within a catheter for delivery to said obstruction and to expand to define the open ends when released from the catheter, said catheter having a radius smaller than a radius of each open end.

4. The device of claim 3 wherein first and second frame components comprise self-expanding material configured to have original and deformed configurations; wherein said self-expanding material is configured to change from said deformed configuration to said original configuration at least by exposure to an activating condition.

5. The device of claim 4 wherein the deformed configuration allows the device to fit within the catheter.

6. The device of claim 1 wherein each body component is attached to a respective guide member substantially along a length of the respective body component.

7. The device of claim 1 wherein the second end is attached to the respective guide member.

8. The device of claim 1 wherein the body components are devoid of any fenestrations.

9. The device of claim 1 wherein at least one body component comprises a woven material of at least one of the following: a polymer, a metal, and any combination thereof.

10. The device of claim 1 wherein the body components comprise a soft and flexible material.

11. The device of claim 1 wherein the body components comprise self-expanding material configured to bias the body components into expanded configurations.

12. The device of claim 1 wherein each body component covers at least a portion of a surface of the respective frame component to which each body component is coupled.

13. The device of claim 1 wherein at least one guide member is adapted to provide a suctioning force.

14. The device of claim 1 wherein the diameter of one frame component is smaller than the diameter of the other frame component.

15. The device of claim 1 wherein at least one frame component comprises an inflatable member.

16. The device of claim 1 further comprises an inflatable member disposed near at least one frame component.

17. The device of claim 1 wherein at least one guide member comprises a body with a channel disposed therein, said body having at least one aperture positioned near an end near the respective capture member.

18. The device of claim 17 wherein the at least one guide member is used to provide a suctioning force.

19. The device of claim 18 wherein the at least one guide member is used to deliver a therapeutic substance to said obstruction.

20. A device to remove an obstruction in a lumen comprising:
a first capture member
a second capture member;
each capture member comprises an open end and a tapered end, wherein said open end comprises a frame component coupled to a body component, said body component extending between said open end and said tapered end;
a first guide member coupled to said first capture member at an open end and a tapered end of a first body component;
a second guide member coupled to said second capture member at an open end and a tapered end of a second body component;
wherein said first capture member and said second capture member are slidably coupled to each other, said slidable coupling comprises said first guide member disposed in said second guide member;
wherein first and second frame components are slidably coupled to the first and second guide members, respectively, thereby allowing the first and second frame components to be moved independently of the first and second guide members.

21. The device of claim 20, wherein the body components are devoid of any fenestrations.

22. The device of claim 20, wherein at least one body component comprises a woven material of at least one of the following: a polymer, a metal, and any combination thereof.

* * * * *